(12) United States Patent
Lowe

(10) Patent No.: US 8,066,179 B2
(45) Date of Patent: Nov. 29, 2011

(54) LIVESTOCK BREEDING AND MANAGEMENT SYSTEM

(75) Inventor: Roger Lowe, Mt Helen (AU)

(73) Assignee: Breedcare Pty Ltd., Mount Helen (AU)

( * ) Notice: Subject to any disclaimer, the term of this patent is extended or adjusted under 35 U.S.C. 154(b) by 998 days.

(21) Appl. No.: 11/937,988

(22) Filed: Nov. 9, 2007

(65) Prior Publication Data

US 2008/0128486 A1  Jun. 5, 2008

(30) Foreign Application Priority Data

Nov. 10, 2006  (AU) ................................. 2006906286

(51) Int. Cl.
*G06F 17/00* (2006.01)
*G06F 19/00* (2006.01)
*G06K 19/00* (2006.01)
*G06Q 30/00* (2006.01)
*A01K 31/19* (2006.01)
*A01K 41/00* (2006.01)
*A01K 29/00* (2006.01)
*G08B 13/14* (2006.01)
*G08B 23/00* (2006.01)

(52) U.S. Cl. ........ 235/375; 235/487; 235/385; 119/300; 119/174; 340/572.1; 340/573.1

(58) Field of Classification Search ............... 119/51.02, 119/174, 300–312, 712; 340/572.1, 573.1, 340/573.3, 500, 501; 235/449, 451, 435, 235/487, 375, 385, 472.01

See application file for complete search history.

(56) References Cited

U.S. PATENT DOCUMENTS

| | | | | |
|---|---|---|---|---|
| 1,237,983 A * | 8/1917 | Werner | .......................... | 600/551 |
| 3,297,020 A * | 1/1967 | Mathiesen | ..................... | 600/551 |
| 3,844,273 A * | 10/1974 | Polson | .......................... | 600/551 |
| 3,878,845 A * | 4/1975 | Schacht | ......................... | 128/883 |
| 4,206,766 A * | 6/1980 | Bielka | ........................... | 600/551 |
| 4,239,018 A * | 12/1980 | Griffin et al. | ................ | 600/551 |
| 4,503,808 A * | 3/1985 | McAlister | ..................... | 600/551 |
| 4,504,808 A | 3/1985 | Basnett | | |
| 4,651,137 A * | 3/1987 | Zartman | ..................... | 340/573.3 |
| 4,846,106 A * | 7/1989 | Leonardo | ...................... | 600/551 |
| 5,322,034 A * | 6/1994 | Willham et al. | ........... | 340/10.41 |
| 5,542,431 A * | 8/1996 | Starzl et al. | ................... | 600/551 |
| 6,049,280 A * | 4/2000 | Andersson | ................ | 340/573.3 |

(Continued)

FOREIGN PATENT DOCUMENTS

WO    WO 03/045273 A1    6/2003

(Continued)

*Primary Examiner* — Daniel Walsh

(74) *Attorney, Agent, or Firm* — Westerman, Hattori, Daniels & Adrian, LLP

(57) ABSTRACT

A method and system for livestock breeding and management for use with a herd where each female animal carries a radio frequency identification (RFID) tag. The system comprises a herd management system and one or more breeding activity monitors to be carried by each male animal. Each breeding activity monitor is adapted to detect when the male animal is mounting a female animal based on the body position of the male animal, read identification data from the RFID tag carried by the mounted female animal, and generate breeding activity data including the identification data of the mounted female animal, mounting male animal and timing data for each mounting for output to the herd management system. The herd management system is adapted to process breeding activity data output from the breeding activity monitors to generate herd management data.

24 Claims, 6 Drawing Sheets

U.S. PATENT DOCUMENTS

| | | |
|---|---|---|
| 6,236,318 B1 | 5/2001 | Yang et al. |
| 6,470,338 B1* | 10/2002 | Rizzo et al. ............................ 1/1 |
| 6,664,897 B2* | 12/2003 | Pape et al. ..................... 340/573.3 |
| 7,918,185 B2* | 4/2011 | Araki et al. ..................... 119/174 |
| 2002/0124803 A1* | 9/2002 | Chen et al. ................. 119/14.08 |
| 2002/0158765 A1* | 10/2002 | Pape et al. ................... 340/573.3 |
| 2002/0169623 A1* | 11/2002 | Call et al. ............................ 705/1 |
| 2003/0000479 A1* | 1/2003 | Starr ............................ 119/174 |
| 2003/0066491 A1* | 4/2003 | Stampe ........................ 119/174 |
| 2003/0069515 A1* | 4/2003 | Theelen et al. ............... 600/551 |
| 2003/0137431 A1* | 7/2003 | Hogan ..................... 340/870.11 |
| 2003/0140865 A1* | 7/2003 | Fuqua ............................ 119/174 |
| 2003/0177025 A1* | 9/2003 | Curkendall et al. ............... 705/1 |
| 2003/0228604 A1* | 12/2003 | Plastow et al. ..................... 435/6 |
| 2003/0229452 A1* | 12/2003 | Lewis et al. ..................... 702/19 |
| 2005/0133593 A1* | 6/2005 | Estakhri et al. ............... 235/381 |
| 2006/0038010 A1* | 2/2006 | Lucas ........................... 235/385 |
| 2006/0187048 A1* | 8/2006 | Curkendall et al. ........ 340/572.4 |
| 2006/0202835 A1* | 9/2006 | Thibault .................... 340/573.1 |
| 2007/0288249 A1* | 12/2007 | Rowe et al. ....................... 705/1 |
| 2008/0017124 A1* | 1/2008 | Fuqua ............................ 119/174 |
| 2008/0030348 A1* | 2/2008 | Pape et al. .................. 340/573.3 |
| 2008/0059534 A1* | 3/2008 | Stroman et al. ............. 707/104.1 |
| 2008/0066693 A1* | 3/2008 | Bocquier ...................... 119/859 |
| 2008/0218357 A1* | 9/2008 | March et al. ............... 340/573.1 |
| 2008/0291030 A1* | 11/2008 | Pape et al. .................. 340/573.3 |
| 2009/0138950 A1* | 5/2009 | Hird .................................. 726/7 |
| 2009/0145364 A1* | 6/2009 | Hardy et al. ............... 119/14.04 |
| 2010/0030036 A1* | 2/2010 | Mottram et al. .............. 600/301 |

FOREIGN PATENT DOCUMENTS

| | | |
|---|---|---|
| WO | WO 2005/065574 A1 | 7/2005 |

* cited by examiner

LIVESTOCK BREEDING AND MANAGEMENT SYSTEM

FIELD OF THE INVENTION

The field of the present invention is livestock breeding, monitoring and management. One example of an application for an embodiment of the present invention is for monitoring the breeding activities of cattle.

BACKGROUND OF THE INVENTION

In the livestock industry productivity and profitability is reduced by animals which do not conceive each breeding season. With every breeding herd, it is important to maximize the asset utilization throughout the breeding cycle. Any female not falling pregnant, is in fact a non productive asset. Depending on oestrus cycle and bull availability, this can leave a female unproductive during an extended time period. The end result is lost revenue due to lost offspring production.

Known methods to monitor conception in a breeding herd include rounding up the animals and having a veterinary surgeon (Vet) perform a physical examination of every female animal, often called the "Palpation" method. The veterinary surgeon checks for swelling of the uterus and ovary. This can be a time consuming and costly task for both farmer and vet depending on the size of the herd being examined. Analysis of blood samples for progesterone can also be used to determine whether animals have conceived, this can also be time consuming and expensive.

Actions to increase the conception rate in a herd can involve either providing more conception opportunities for an animal or providing the conception opportunities at or around an optimal time in the oestrus cycle when the animal is most likely to conceive (in heat).

For example, to provide more conception opportunities a farmer can either reduce the roaming distance or increase the male to female ratio of the herd and simply let nature take its course. Each of these options increases the likelihood of a male animal being around a female animal when she is in heat, thereby potentially increasing the odds of a successful conception.

Determining when an animal is in heat can enable a farmer to bring the female animal into proximity with a male animal for natural breeding or artificially inseminate the animal at an optimum time. Artificial Insemination is traditionally used to guarantee a particular attribute of the male animal not owned by the farmer. It is still not totally effective with an approximate 50% conception rate. For the majority of farms, this approach is limited or impractical.

Known methods to determine when an animal is in heat include:
  observation of the animals by the farmer to look for signs of heat, such as mounting of the animal by other animals, swelling or reddening of the vulva, mucus discharge, restlessness or aggressive behaviour, and shortened feeding time;
  paint, chalk or dye marking which is traditionally seen in sheep herds, where the ram has a paint/chalk marker attached to the under belly, when the ram mounts a ewe a mark is left on the mounted ewe and can be observed by the farmer, the effectiveness of this method is dependent on the climate; and
  mount detecting devices which are pressure sensitive devices glued to the back or rear of the female animal, when the animal is mounted by another the device changes colour or provides some other indication of the mounting which can then be observed by the farmer. All of these methods depend on some physical observation by the farmer and although the observation can detect when an animal is in heat, another check is required after mating or insemination to determine whether the animal has conceived. Whilst it can be determined whether an animal has conceived, it is difficult to determine how easily the animal conceived, for example how may times did the male need to service the female for her to become pregnant. Further, unless artificial insemination is used or there is only one fertile male animal in the herd, tracking of the parentage of the offspring can be difficult or impossible.

There is a need for a system which enables a more reliable monitoring of the oestrus cycles and breeding activities of livestock.

SUMMARY OF THE INVENTION

According to one aspect of the present invention there is provided a system for livestock breeding and management for use with a herd where each female animal carries a radio frequency identification (RFID) tag, the system comprising:
  a herd management system; and
  one or more breeding activity monitors to be carried by each male animal, each breeding activity monitor is adapted to:
    (i) detect when the male animal is mounting a female animal based on the body position of the male animal;
    (ii) read identification data from the RFID tag carried by the mounted female animal; and
    (iii) generate breeding activity data including the identification data of the mounted female animal, mounting male animal and timing data for each mounting for output to the herd management system,
wherein the herd management system is adapted to process breeding activity data output from the one or more breeding activity monitors to generate herd management data.

According to another aspect of the present invention there is provided a breeding activity monitor adapted to be carried by an animal for use in a herd where animals are provided with radio frequency identification (RFID) tags, the apparatus comprising:
  a radio frequency identification (RFID) tag reader for reading identification data from an RFID tag secured to another animal in the herd;
  a mount detector to determine when the animal is mounting another animal based on the body position of the animal;
  a processor for processing the data from the RFID tag reader, processing data from the mount detector to generate breeding activity data including the identification data of the mounted animal, mounting animal and timing data for each breeding activity; and
  a communication interface to enable output of the acquired breeding activity data by an external device.

A method for monitoring breeding activity in a herd where each female animal carries a radio frequency identification (RFID) tag, the method comprising the steps of:
  attaching a breeding activity monitor to be carried by the animal to each breeding male animal in the herd;
  detecting by the breeding activity monitor attached when the male animal mounts a female animal based on the body position of the male animal; for each mount:
  reading identification data from the RFID tag of the mounted female animal; and generating breeding activity data including the identification data for the mounted female animal, mounting male animal, timing data for the mounting, and;

processing the breeding activity data output from one or more breeding data activity monitors to generate herd management data.

According to another aspect of the present invention there is provided a method for analysing breeding activity data to provide herd management data comprising the steps of:

acquiring breeding activity data including mounting data for a herd including for each mounting at least identification data for the mounted female animal and timing data;

analysing the breeding activity data to determine one or more of:

conception data for each female animal;

birth date estimates for each pregnant female animal;

male animal work rates;

conception success rate data for each male animal;

fertility and ease of impregnation data for each female animal; and offspring family data, and outputting the determined processing results as herd management information.

According to another aspect of the present invention there is provided a herd management system for analysing breeding activity data including mounting data including for each mounting at least identification data for the mounted female animal and timing data, the system comprising:

an input interface adapted to enable at least breeding activity data to be manually or automatically entered into the system;

a processor adapted to process the input breeding activity data to produce herd management data;

a memory for storing breeding activity data and herd management data; and an output interface, wherein the processing of the breeding activity data provides herd management data including one or more of:

conception data for each female animal;

birth date estimates for each pregnant female animal;

male animal work rates;

conception success rate data for each male animal;

fertility and ease of impregnation data for each female animal; and offspring family data.

Preferably the mounting data further includes identification data for a male animal mounting the female animal.

Preferably the processing of the breeding activity data provides herd management data including one or more of:

conception data for each female animal;

birth date estimates for each pregnant female animal;

male animal work rates;

conception success rates for each male animal;

fertility and ease of impregnation data for each female animal; and offspring family data.

Conception by a female animal can be predicted and conception data for a female animal can be generated based on analysis of the mounting activity for the female animal and oestrus cycle data for the female animal. For example, where a female animal has been mounted in the first oestrus cycle, the breeding activity data is processed to determine whether or not an available male animal has not mounted the female animal within a duration longer than one oestrus cycle since a previous mounting of the female animal. The male not returning to the female when it is expected that she was in heat is an indicator of the likelihood of pregnancy, when this is determined the conception data for the female animal is updated to indicate a high likelihood of conception. Statistical analysis of the mounting data optionally supplemented with data, such as historical fertility data for the female and male animals or typical fertility and oestrus cycles for the particular breed, can be used to determine a probability of conception. Conception can be confirmed by a veterinary inspection if deemed warranted.

Preferably the likely birth date for a pregnant female animal is determined based on data relating to the last mountings by a male animal prior to conception being determined and a typical gestation period for that breed of animal.

A measure of the ease of impregnation of a female animal can be generated based on the number of mountings by a male animal prior to conception. Another measure of the fertility of a female animal can be generated based on the number of oestrus cycles experienced by the female animal and the number of mountings between the birth of one offspring and the conception of another offspring. The fertility of a female animal can be determined relative to other female animals. Measures of the fertility of a female animal can be further based on fertility data for a male animal which impregnated the female animal.

The male animal work rate can be determined based on the number of female animals being mounted by the male animal during a given period. The determination of the work rate can be further based on the number of female animals impregnated by the male animal during the given period. The likely male animal conception rate can be determined based on the number of female animals impregnated by the male animal during a given period.

Offspring family data can be generated based on the identification data for the female animal and the identity of a male animal last mounting the female animal prior to conception being determined. Analysis of this data can determine the likely parentage of the offspring. Where multiple males have mounted the female during a single day the parenthood data may be qualified by a probability of fatherhood by each of the male animals.

Preferably each breeding activity monitor is provided with a wireless communication interface whereby the breeding activity data is transmitted to the herd management system for processing.

The system can further comprise one or more wireless base stations located in an area where the herd roams such that, when a breeding activity monitor is within transmission range of a base station, breeding activity data is transmitted wirelessly to the base station for subsequent transmission to the herd management system. In one embodiment each base station transmits the breeding activity data to the herd management system via a communication network. Alternatively each base station could be adapted to store breeding activity data for subsequent downloading by a farmer. For example, each base station can include a wireless transmitter for transmission of breeding activity data wirelessly to a portable device such as a wireless enabled laptop computer, personal digital assistant, mobile phone or the like.

Embodiments of the invention can be adapted to suit any livestock where the male animal mounts the female animal. Examples of applications envisaged within the scope of the present invention include cattle, sheep, horses, pigs, goats, camels, alpacas, deer etc.

DETAILED DESCRIPTION

Figure 1:
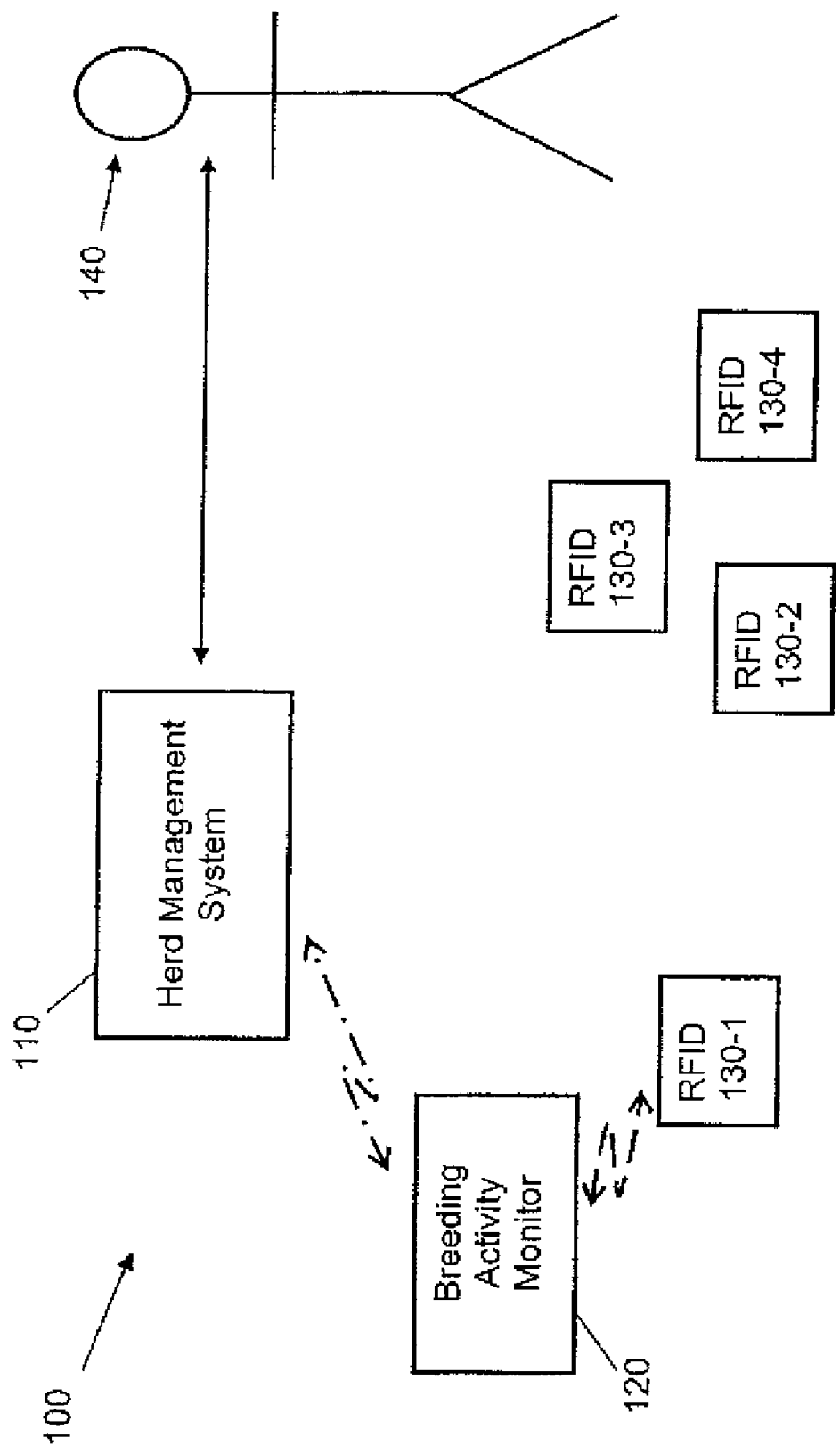
FIG. 1 is a bock diagram of a livestock breeding and management system according to an embodiment of the present invention.

A block diagram of an embodiment of the livestock breeding and management system of the present invention is shown in FIG. 1. The livestock breeding and management system 100 comprises a herd management system 110 and one or more breeding activity monitors 120 for carrying by a male animal. The livestock breeding and management system of embodiments of the present invention is designed to be used in herds where at least each female animal in the herd is provided with a radio frequency identification (RFID) tag 130. The breeding activity monitor 120 is adapted to detect when the animal carrying the monitor mounts another animal based on the body position and relative proximity of the two animals and reads identification data from the RFID tag 130-1 on the mounted animal. The breeding activity monitor 120 stores breeding activity data including timing data for the mounting and the identification data for the mounted animal. The herd management system is adapted to process breeding activity data acquired from one or more breeding activity monitors 120 to provide herd management data to the farmer 140.

Detailed information for each breeding activity can be stored by the breeding activity monitor 120 and provided to the herd management system for processing. This enables the herd management system 110 to perform detailed analysis of the breeding activity, across the herd or for individual animals, and provide herd management information relating to the fertility of individual animals and profitability of the herd to the farmer.

The embodiments of the invention will now be discussed using an example where the herd management system is used for a herd of cattle. For this example the breeding female animals, cows and heifers, will be referred to as breeders and the breeding male animals referred to as bulls, a cattle herd may also include juvenile animals not yet ready to breed such as calves and yearlings and may also include sterile male animals such as steers, for the purpose of this example breeders and bulls will be discussed. Although embodiments of the present invention are described in application to cattle breeding, embodiments of the invention may equally be applied for other species of livestock, for example sheep, horses, pigs, goats, camels, alpacas, deer or the like. Embodiments of the invention may be adapted to be suitable to any species of livestock where a male animal mounts a female animal, usually from the rear. Words such as bull, cow, herd etc should be considered interchangeable with similar common words in relation to other species of livestock, for example ram, ewe, flock etc in relation to sheep.

Figure 2:
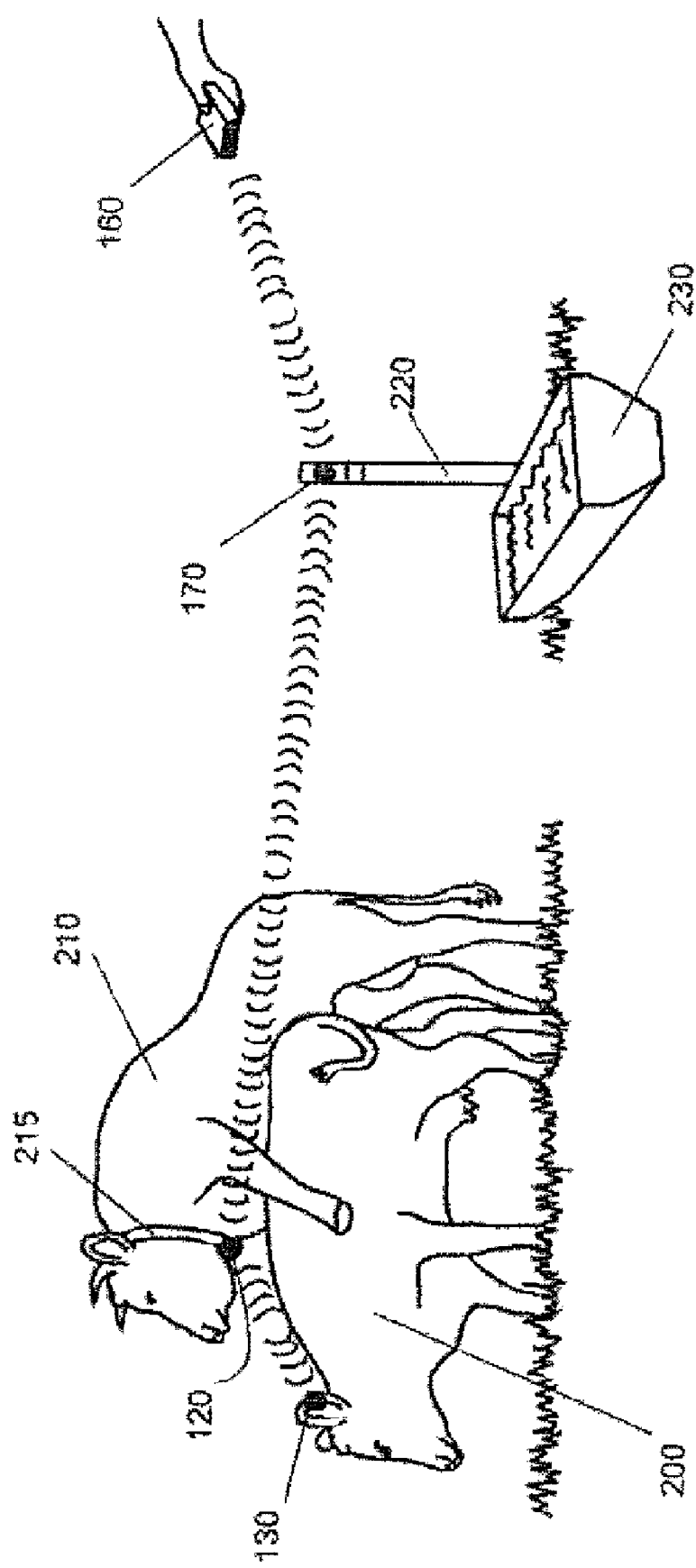
FIG. 2 illustrates an embodiment of the present invention used for cattle herds.
Figure 3:
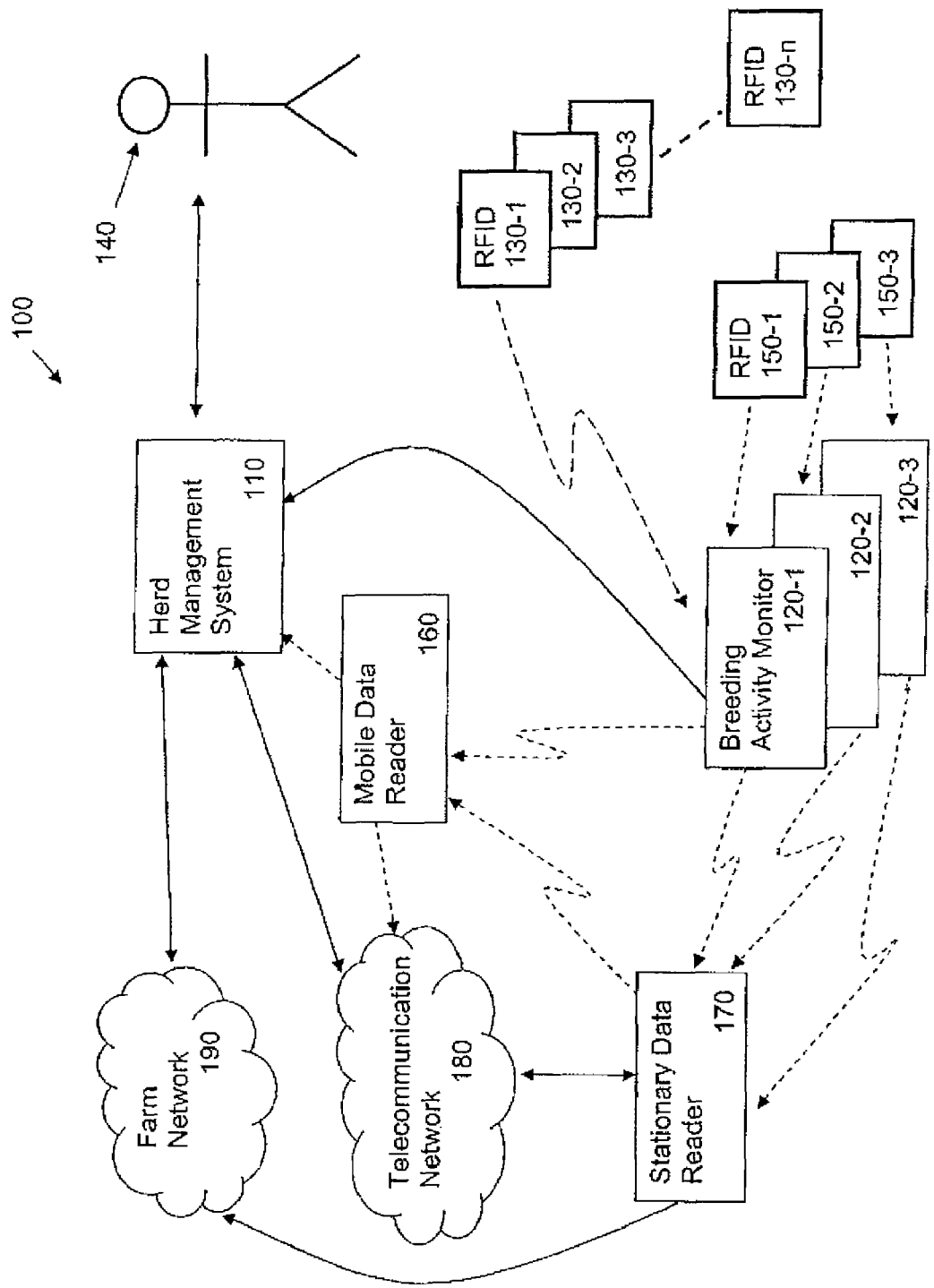
FIG. 3 is a bock diagram of a livestock breeding and management system according to another embodiment of the present invention.
Figure 4:
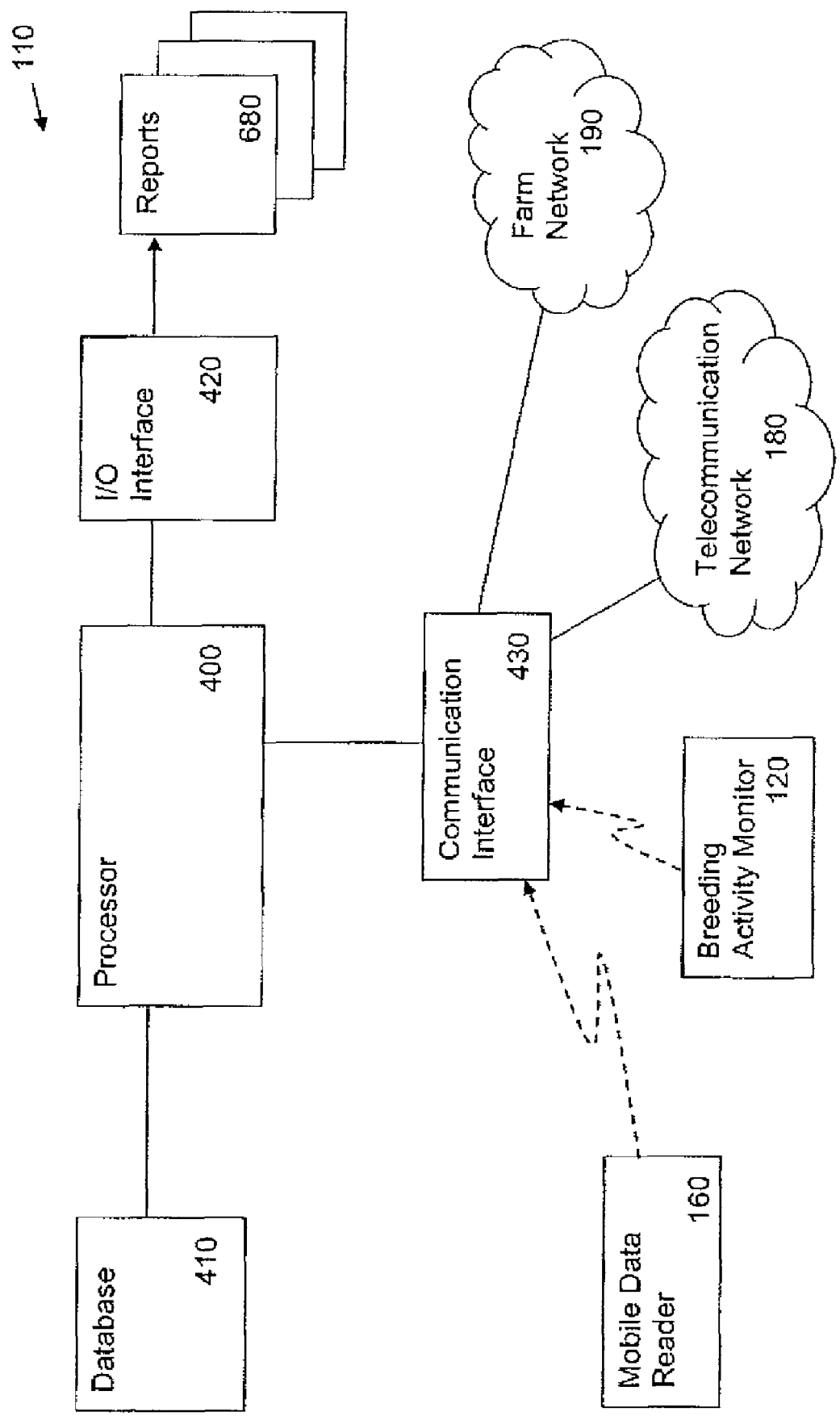
FIG. 4 is a functional block diagram of a herd management system according to an embodiment of the present invention.

An embodiment of the invention for use in a cattle herd is illustrated in FIG. 2. Each breeder 200 in the herd has an RFID ear tag 130. In the preferred embodiment the ear tag is a standard tag, such as is used in the Australian National Livestock Identification System (NLIS) which utilises Radio Frequency Identification (RFID) ear tags to provide a unique reference point for all cattle, however customised tags may also be used. The advantage of using an NLIS tag is that these tags are required to be attached to each animal in the herd under the NLIS program, so the herd breeding and management system simply uses the ear tags already provided on the cattle. Therefore no additional action or expense is incurred by the farmer/producer in relation to the RFID tags for the breeders.

Each bull 210 is provided with a breeding activity monitor 120 attached to a collar 215 worn by the bull 210. A collar 215 is suitable for use on a bull however a halter or other type of harness may also be used to secure the monitor 120 to the bull. The means for carrying the breeding activity monitor 120 can be modified to suit the particular animals, for example a collar may be best suited for sheep, goats and cattle whereas a halter may be more suitable for horses, deer or alpacas.

Figure 5:
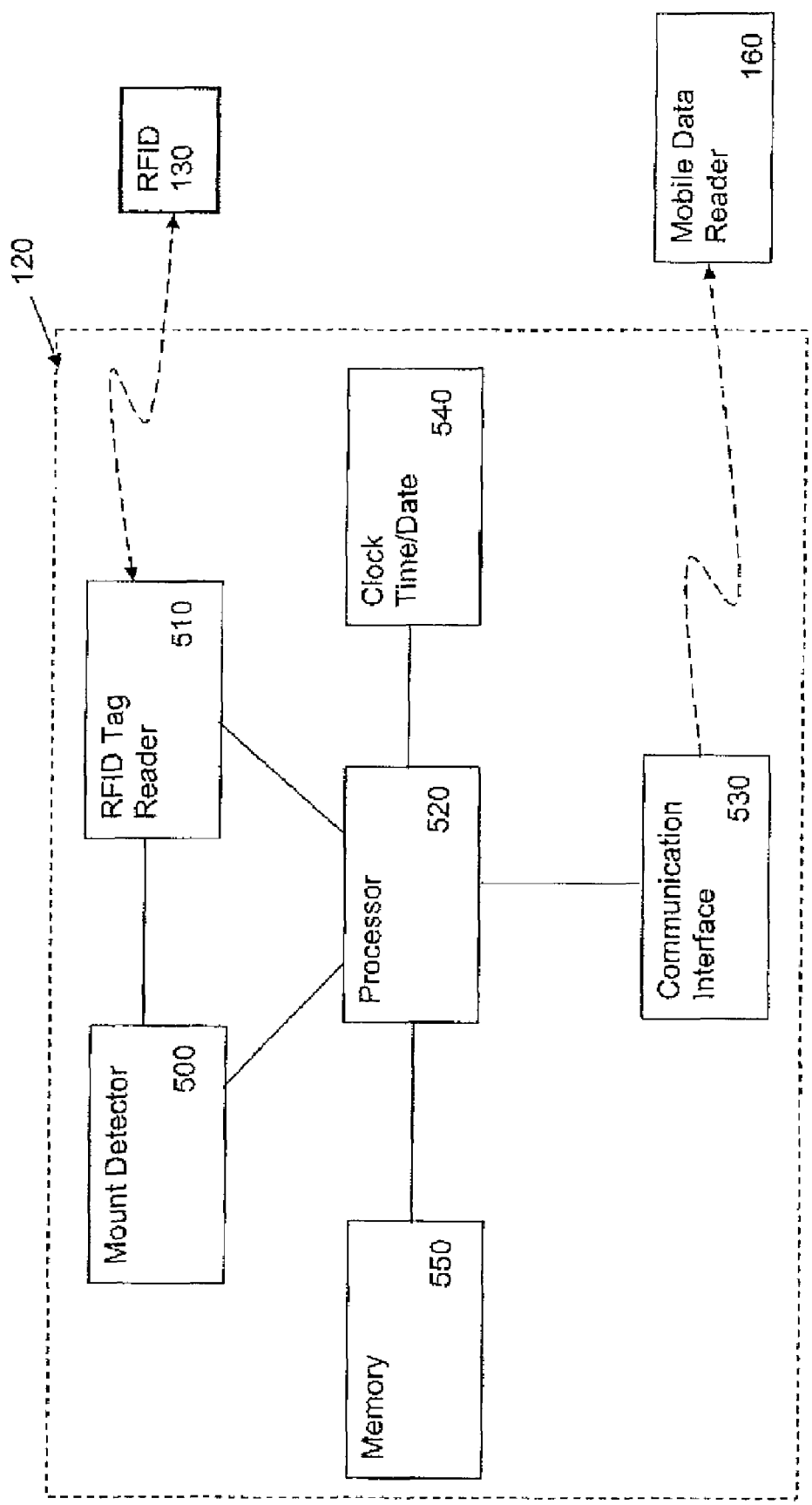
FIG. 5 is a functional block diagram of a breeding activity monitor according to an embodiment of the present invention.

A functional block diagram of an embodiment the breeding activity monitor 120 is shown in FIG. 5. The breeding activity monitor 120 of the preferred embodiment comprises: a mount detector 500, an RFID tag reader 510, a processor 520, a communication interface 530, a clock or timer 540 and memory 550. The processor 520 acts as a controller for the breeding activity monitor and performs functions such as analysis of data provided by the mount detector 500, RFID tag reader 510 and processing of this information for storage and transmission via the communication interface 530.

The breeding activity monitor is powered by a suitable power supply (not shown) any suitable power supply may be used. It is desirable to use a renewable power supply to enable the apparatus to be deployed on the male animal for an extended period of time for example, a rechargeable battery, charged using a solar energy trickle charger. Alternatively where technology is available to utilise other natural sources of energy such as the movement or body heat of the animal such energy sources may be utilise in the power supply to extend the field life of the apparatus and minimise the risk of data loss due to flat batteries.

The mount detector 500 in the breeding activity monitor 120 will detect when a mounting action has happened. This mount detection can be determined based on the body position of the bull and can also take into consideration the length of time the position is held, for example the elevation and angle of the Bull's body can be monitored using an angle and motion sensor, such as an inertial sensor. The bull's activity could be constantly monitored or a sensor be used to trigger the breeding activity monitor out of a standby/power saving mode say by the bull jumping, similarly to jumping to mount the breeder, the movement of the bull is then monitored to determine whether the bull's body is in a mount position. The length of time the bulls body remains in the mount position can also be used to distinguish a servicing mount from a false mount or other movement such as a jump where the bull has not held the mount position long enough to service a breeder.

Reading of the RFID tag of the mounted animal with the RFID tag reader 510 can optionally be used confirm the mounting. For example, if the bull has not mounted a breeder and is instead say standing with its front legs on a boulder or platform, there will be no breeder RFID tag in the proximity of the RFID tag reader 510, so the bull 210 cannot be mounting a breeder 200 and the prediction of a mount can be disregarded by the processor.

Alternatively the mounting position may be determined from the relative position and proximity of the breeding activity monitor 120 to the breeder's RFID tag 130 determined by the reading taken by the RFID tag reader 510. When the bull 210 is mounting the breeder 200 the RFID tag will be within a certain arc or sector of the range of the RFID reader 510, for example for the bull 210 the breeder's 200 RFID tag 130 is within a 30° arc forward of the RFID tag reader 510 in the breeding activity monitor 120 on the bull 210. The arc and range forward of the RFID tag reader aerial can vary depending on the breed of animal, due to the differing sizes of animals, for example a breeding activity monitor for use on sheep will require a shorter reading range for that used for cattle due to the relative sizes of sheep and cattle. Similarly the required reading range can vary for different breeds of cattle. Thus it is envisaged that the range and arc forward of the RFID tag reader may be variable in some embodiments of the breeding activity monitor, for example by manually setting read parameters based on guidelines for particular breeds. Alternatively there may be a calibration function provided in the processor to set the appropriate parameters when a mount is detected for the first time. For simpler embodiments, for a mass produced embodiment designed for a particular breed of sheep, a fixed range and arc may be used.

When the bull 210 mounts the breeder 200 as shown in FIG. 2, the identification data for the breeder 200 is read from the breeder's RFID ear tag 130 using the RFID tag reader 510. This data and timing data for the mounting, provided by the clock 540, are stored in memory 550. In the preferred embodiment the timing data provided by the clock 540 includes the time and date of the mounting. Alternatively the clock 540 could be a countdown timer or the like which provides relative timing data which is converted to absolute time and date data by the herd management system when it is downloaded, say based on the date and time the breeding activity monitor was placed on the bull or from the last download of breeding activity data for the breeding activity monitor.

Optional data, such as the duration of the mounting and the identity of the bull, may also be recorded. For example the duration of the mounting could indicate whether the mounting was too short for the bull to service the breeder, indicating a false mount, or to monitor the time taken by the bull to service the breeder. In an embodiment of the breeding activity monitor 120 which is not programmed with the bull's identification data, the bull's RFID ear tag could also be read using the RFID tag reader 510 for each mounting to record this data.

The breeding activity data collected by the breeding activity monitor 120 is downloaded using the communication interface 530 to a herd management system 110 for processing. The communication interface 530 may enable the data to be downloaded directly from the monitor 120, when it is removed from the bull or when the bull is restrained, or comprise a wireless communication interface, such as a Bluetooth, to enable the breeding activity data to be downloaded without requiring any contact with the bull. For example as the bull is being moved from one paddock to another and the farmer is near the bull the breeding activity data could be transmitted by the wireless communication interface to wireless mobile data reader 160 carried by the farmer.

In the embodiment shown in FIG. 2 the breeding activity monitor 120 is provided with a wireless communication interface 530. The breeding activity data can be downloaded via stationary or mobile wireless data readers. FIG. 2 shows a stationary data reader 170 or base station embedded in a post 220 near a water trough 230. The data reader 170 can download breeding activity data from the breeding activity monitor 120 using the wireless communication interface 530 each time the bull 210 is in range of the data reader 170, the data is stored in the stationary data reader 170 for retrieval by the farmer using a mobile data reader 160.

The stationary data reader 170 can be placed in a paddock in an area commonly used by the herd, such as near food or water, so the bull 210 will regularly be in the proximity of the data reader 170 to download breeding activity data. The data from the stationary data reader 170 may be downloaded by the farmer using a mobile data reader 160 at any convenient time so the farmer does not need to be near the bull to download the data. The mobile data reader 160 could be any wireless enabled device, such as a personal digital assistant, laptop computer, mobile phone or the like. Alternatively the mobile data reader 160 may be physically connected to the stationary data reader 170 to download the information, for example the data my be transferred to a memory device such as a memory card, disk, or USB stick when inserted into the stationary data reader 170, or cable to a laptop or other device may be plugged into the stationary data reader 170 to download the data.

Alternatively the stationary data reader 170 may transmit the downloaded breeding activity data directly to the herd management system 110, say via a telecommunication network or a private communication network. Alternatively, where the technology is available, wireless communication may enable the data to be downloaded directly from the breeding activity monitor 120 to the herd management system 110, for example via a telecommunication network.

Optionally, a locating module to provide information regarding the location of the bull, and subsequently the herd, may be provided in the breeding activity monitor. The locating module may use existing location technology, such as global positioning system (GPS) or cellular network based location technology. Similar to the breeding activity data the breeding activity monitor may download position data periodically or in response to interrogation. For example, the breeding activity monitor including a GPS locating module and mobile telecommunication functionality may be interrogated using the mobile telecommunication network to selectively download the breeding activity data or position data. The position data could be used by the herd management system to map and track the movements of the herd based on the location of the bulls.

The herd management system of the preferred embodiment is a software driven system including a database 410 for storing the breeding activity data and a processor 400, such as a personal computer, for providing the data processing functions, data may be input to the system using a communication interface 430, for example for the downloading of breeding activity data, or manual input/output interface 420, for example for the farmer to enter data manually from a memory device or to enter queries or parameters for the processing of the herd management data and for outputting herd management data or reports to the farmer. The herd management system is not limited to using only breeding activity data downloaded from the breeding activity monitors of embodiments of the present invention. The Herd management system can also be used to process breeding activity data obtained using other devices or manually captured and input to the system. Naturally the accuracy of predictions based on the breeding activity data will vary with the amount or accuracy of breeding activity data itself, however, the amount and quality of the data may also be taken into consideration during the data analysis and probabilities indicating the estimated accuracy of the predictions adjusted accordingly.

For the following description of the herd management system it is assumed that data downloaded from the breeding activity monitors of the preferred embodiment. The breeding activity data downloaded to the herd management system 110 from the breeding activity monitors 120 includes the date and time, bull and breeder identification information for each mounting, in its simplest form the data is a record of which bull has serviced which breeders and when such occurred. The duration of each mounting may also be recorded. The functions performed by an embodiment of the herd management system 110 are illustrated in FIG. 6.

Figure 6:
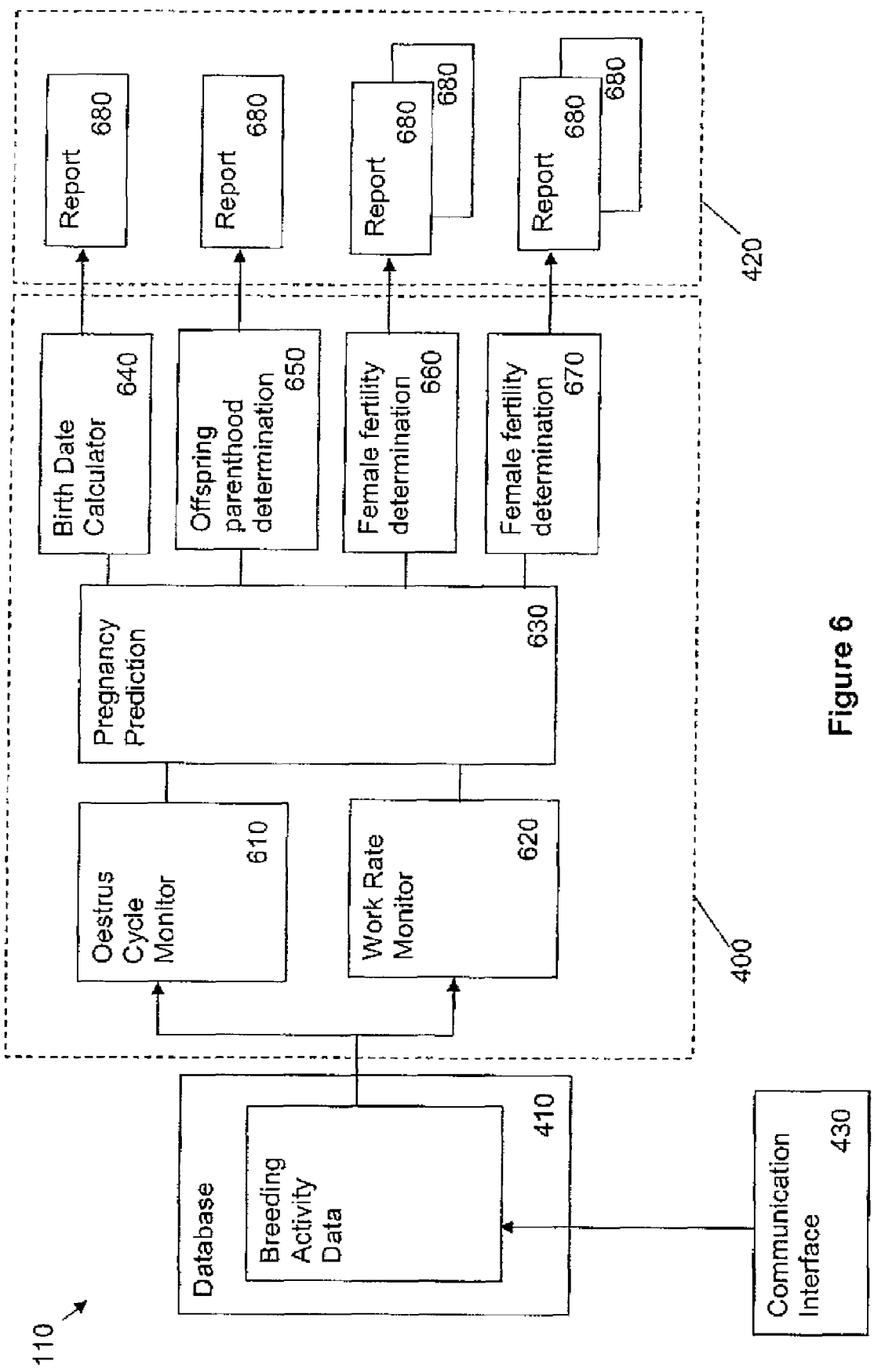
FIG. 6 is a functional block diagram illustrating the processing functions performed in an embodiment of the herd management system.

The herd management system 110 shown in FIG. 6 includes the functions of: Oestrus cycle monitoring 610, male animal work rate monitoring 620, pregnancy prediction 630, birth date prediction 640, offspring parenthood determination 650, female animal fertility determination 660 and male animal fertility determination 670, further functions (not shown) may also be provided such as comparative fertility analysis and comparative health analysis for example comparing data between individual animals, different herds, or different breeding seasons. The analysis can be output to the farmer in a variety of ways such as in response to specific queries or as reports 680 including information output from one or more of the functions.

Better knowledge of the breeding activities of the herd enables the farmer to identify unproductive breeders to cull from the herd or to take action to rectify problems that may affect the conception rate in the herd in order to improve the herd productivity. If the herd management system has stored or has access to historical data for the herd as well as present breeding cycle data, the herd management system can also provide comparative information and highlight changes or anomalies which may indicate problems in the herd.

An example of the breeding activity data stored in a breeding activity monitor is illustrated in table 1 below.

TABLE 1

| BREEDER ID | DATE | TIME |
|---|---|---|
| Cow#1 | 20/7/06 | 08:45 |
| Cow#42 | 20/7/06 | 09:25 |
| Cow#47 | 20/7/06 | 13:57 |
| Cow#1 | 21/7/06 | 09:03 |
| Cow#35 | 21/7/06 | 10:46 |

As each breeding activity monitor is worn by a different bull it is not essential to record a bull identifier for every mounting, as this information can be added when the data is downloaded to the data reader or herd management system.

An example of the breeding activity data downloaded to the herd management system is given below in table 2.

| BULL ID | BREEDER ID | DATE | TIME |
|---|---|---|---|
| Bull#1 | Cow#1 | 20/7/06 | 08:45 |
| Bull#2 | Cow#35 | 20/7/06 | 08:53 |
| Bull#1 | Cow#42 | 20/7/06 | 09:25 |
| Bull#3 | Cow#26 | 20/7/06 | 09:35 |
| Bull#3 | Cow#17 | 20/7/06 | 09:58 |

The duration of each mounting can optionally be recorded by the breeding activity monitor and downloaded to the herd management system. The mount duration may be of interest to a farmer to distinguish between false mounts, say where the breeder had moved away before allowing servicing by the bull, and true mounts of long enough duration for the bull to have serviced the breeder. From the number, frequency and duration of mountings for each breeder, each breeder's oestrus cycle can be monitored by the oestrus cycle monitor 610, for example the length of the oestrus cycle and when the breeder is coming into heat and in standing heat, standing allowing a bull to service her, can be predicted.

Typically for cattle a mount of less than 3 seconds is a false mount. Instead of collecting data regarding the duration of mounts it is possible to exclude data for false mounts, say by requiring the mounting to exceed threshold duration before recording data, such as 3 s, or to simply provide a flag to distinguish true and false mounts in the collected data. Information regarding false mounts can be useful for monitoring when breeders are coming into heat, when a bull may attempt to mount but the breeder may not stay still to allow the mount for the bull to service her, as well as the period in standing heat when they will allow a bull to mount successfully.

The herd management system uses the pregnancy prediction function 630 to analyse the mounting activity data to indicate which breeders are likely to be pregnant and which are not. Determining the likelihood of conception enables a farmer to identify breeders which need to be segregated from the main herd for further work by the bull. Likelihood of conception is determined based on two pieces of data, the servicing activity for the breeder and the oestrus cycle period. If a bull has serviced a breeder and does not return to service the breeder again for more than an oestrus cycle period, say around 21 to 24 days for cattle, then the breeder has most likely conceived from servicing during her last cycle, and the herd management system indicates the breeder as likely to be pregnant in the stored data. Confirmation of the pregnancy can be made through veterinary examination such as palpitation if desired.

The data from the servicing which resulted in conception, otherwise known as a successful crossing, can be used to determine the expected birth date and also to determine the parenthood of the offspring. The birth date is determined by the birth date calculator function 640 based on the date of the last servicing and the gestation period. For example for a cow, adding the typical gestation period of 9 months and 7 days or approximately 280 days to the date of last servicing gives an estimate of the calving date to within 3-4 days either side. This enables a farmer to segregate breeders based on their anticipated birthing dates for closer observation when they near the completion of the gestation period.

The accuracy of the birth date and parenthood predictions will vary depending on the number of mountings and the number of bulls servicing the breeder. In a situation where more than one possible mounting has resulted in the pregnancy or more than one bull has serviced the breeder during the oestrus cycle where conception occurred the herd management system may provide additional data indicating the probability of parenthood by each bull and similarly probability of expected birth dates based on the servicing data.

The herd management system can provide data regarding the likely lineage or parenthood of the offspring, such as which bull sired which calf. The offspring parenthood determination function 650 determines the likely sire of the offspring based on the conception data. Knowledge of the likely parenthood of offspring can be useful in situations where there is potentially more than one male animal with the female animals. Herds are sometimes segregated into breeding groups with one bull per paddock so sires can be determined based on the breeding group, however if a bull escapes its assigned paddock or if breeders are moved between breeding groups to have exposure to multiple bulls, normally it would not be possible, or at least be difficult, to track which male sired which offspring. Similarly, where the herd is not segregated into breeding groups, which often occurs on larger properties or for different types of animals, such as flocks of sheep or goats, where females may be serviced by several males, normally the sire of offspring would not be known. As described above in relation to conception data, where more than one male animal services a female while she is in heat, the parenthood prediction provides only a likelihood or probability of parenthood by a particular sire based on statistical analysis of the breeding activity data. For example, if multiple males mount a single female in a day/week we can only then predict the likely linage, however a probability indicating the relative likelihood of each male being the sire may be provided by the herd management system. Once the calf is born the actual birth day may be input back into the herd management system to re-calculate the probability of parenthood. This may significantly improve the accuracy of the prediction particularly if the breeder was serviced days apart by different males.

Knowledge of the lineage of offspring can be useful for predicting what characteristics that may be inherited by the offspring to predict the suitability for various purposes or value of the offspring. For example, if calves are to be integrated back into the breeding stock, data will be available to predict potential fertility based on the fertility data from the parents. This data also enables a farmer to minimise in-breeding, by allowing for quarantining against an offspring being mated back against its sire. Alternatively in animals which are bread for certain characteristics, such as merino sheep for the quality of their wool, the parentage of a lamb may be used to predict the potential quality of its fleece and value of the lamb which may be used to make decisions regarding which lambs to maintain in the flock and which to sell or cull.

The herd management system can provide early indication of potential breeder fertility problems. If a breeder is not pregnant and is not being serviced then there may be a problem with the breeder's oestrus cycle or some other reason why the bull(s) are not servicing her, such as disease or infection. Variations in a breeder's oestrus cycle can also be an indicator of fertility problems. If such problems occur in a number of the breeders in the herd this may indicate a problem to do with the farm environment rather than just the health of individual animals.

The oestrus cycle monitor 610 can determine whether a breeder is not being serviced by comparing the identities of the breeders in the herd, from a stored list, with the identities of the breeders from the downloaded breeding activity data. The absence of a breeder's identity in the breeding activity data indicates she is not being serviced by any bulls. A list of un-serviced breeders can also be compared with a list of breeders identified as pregnant to exclude any pregnant breeders from the list. The herd management system can provide a report of these un-serviced breeders to the farmer identifying them as potentially having fertility problems.

The length of a breeder's oestrus cycle can be determined from the mounting activity, for example the duration between two different periods of standing heat where the breeder has allowed a bull to mount her. This information can be compared with typical oestrus cycle parameters for the breed to identify an anomalous oestrus cycle which indicates potential fertility problems.

Comparing data from the present breeding season with historical data recorded in previous breeding seasons can also be used to identify variations in oestrus cycles for animals in the herd. Variation in oestrus cycles may be natural, for example caused by the natural development to sexual maturity and aging of the breeder, or have other causes which may affect the breeder's fertility. By comparing the breeders' oestrus cycle data for the current season with historical oestrus data for the herd and/or typical oestrus cycle parameters for the breed of animals, the oestrus cycle monitor function 610 can be used to identify any breeders with oestrus cycles which fall outside expected or desired parameters which may indicate fertility problems.

Early identification of potential fertility problems enables the farmer to take action, such as the farmer or the vet inspecting individual animals for disease, injury, infection or problems caused by a previous birth such as a retained placenta. Alternatively, if there is a wide spread problem, affecting several or many animals in the herd, this may indicate environmental factors are affecting the herd, such as malnutrition during a drought.

Analysing how many times a breeder needs to be serviced to conceive can also be of value to the farmer, this is one of the measures used in the female animal fertility determination function 660. Typically a farmer will know that a breeder conceived by the resulting offspring, but is not able to determine how easily the breeder conceived. For example, if a breeder regularly conceives after being serviced only once or twice by the bull then she is a very valuable breeder. However, if a breeder needs to be serviced say 4 or 5 times before conception, even if she conceives each season she is requiring more effort from the bull to produce each calf which can have the effect of reducing the number of other breeders serviced by the bull which may, in turn, lower the overall productivity rate in the herd.

The breeding activity data also enables the farmer to develop a better understanding of the capabilities and activities of the bulls in the herd and the fertility of each bull. The herd management system can analyse the breeding activity data to determine how often each bull is servicing each breeder, using the work rate monitor function 620 and the conception success rate for the bull based on conception data output by the pregnancy prediction function 630. If a bull is servicing a large number of breeders but some do not conceive it is possible the breeders are not very fertile or barren or the bull may not be sufficiently fertile to impregnate all the breeders he is servicing in the time period. For example, a bull should be sufficiently fertile to impregnate 30 to 50 breeders during one breeding season. A lower conception rate can indicate fertility problems for the bull. The male animal fertility determination function 670 analyses this information to measure the bulls' fertility.

The bull work rate is a measure of the number of breeders in the herd the bull will service within a given period. The work rate monitor function 620 determines the work rate from the breeding activity data by comparing the servicing data recorded during a given period, say 21 to 24 days which is approximately one oestrus cycle for cows, with the list of breeders available to the bull stored in the herd management system. The bull should be servicing each available breeder, who is cycling, during this period. If the bull is not servicing each breeder within this time period, then this could indicate the bull has a medical problem, or simply does not have the stamina to service the number of breeders he is presented with. The bull work rate could also be measured over a longer time period, for example 40 to 60 days or around 2 or 3 oestrus cycles, to minimise the impact of "stress" periods, such as where multiple breeders simultaneously come into heat so the bull may not be able to service all the breeders in heat due to fatigue, or to discount injury.

A shorter work rate monitoring period enables decisions to be made earlier as to whether the bull is able to perform sufficiently to service the breeders in the herd or whether another bull is required or some other action needs to be taken.

Another measure of male animal fertility is the conception rate which can also include a measure of the number of times a bull needed to service a breeder for her to conceive. This measure is calculated by the male animal fertility determination function 670 based on conception information and servicing data. For example, a first bull which has a high rate of successful conceptions after servicing each breeder only once or twice is more desirable in a herd than a second bull which needs to service each breeder 3 or 4 before conception. The first bull can be spread around more than the second bull as the first bull does not need to service each breeder as many times. A bull which can service 45 breeders as effectively as another who can service 35 in a breeding cycle is more desirable for larger herds.

The relative breeder fertility can also be taken into account when determining bull fertility. Where data is available regarding relative breeder fertility, such as relative fertility measures determined by the female animal fertility determination function 660 or data from previous breeding seasons, this data can be used to apply a weighting to the measured conception information. For example, if a breeder is known to be less fertile and typically required to be serviced 3 to 4 times before conception in previous breeding seasons, and she conceives to a bull after only one servicing, this conception may be given a higher weighting in the bulls fertility measure processing than a conception after only one servicing for a breeder known to typically conceive with only one servicing.

The fertility predictions are based on statistical analysis of the breeding activity of the herd. Combinations of the above measures can be analysed to provide measures of the fertility of the animals and to predict future breeding behaviour. The above description provides some examples of the way various aspects of the breeding activity may be determined and compared, however, further algorithms for analysis and statistical processing of the gathered breeding activity data and comparison of the various measures to provide relative and objective measures of fertility are envisaged within the scope of the present invention.

Comparative bull performance can also be determined by comparing conception rates and work rates of each bull on the property against others in different herds.

Bull fertility and work rate data is of use to farmers when determining the required ratio of bulls to breeders in the herd to maximise or optimise productivity. Using the above example a farmer would only need 8 bulls who are more efficient and have a higher success rate to service 350 breeders whereas 10 less efficient bulls may be needed, thus the capital cost for each calf produced is lowered in a herd with more efficient bulls and lower bull to breeder ratio. With knowledge of the bull efficiency the farmer can adjust the bull to breeder ratio in the herd to optimise production.

The herd management system can also process the breeding activity data to determine mating patterns which enable a farmer to be onsite at the time which provides a higher potential to physically monitor the mating activity, if the farmer actually wishes to physically monitor the mating activity. Visual inspection can provide farmers with "peace of mind" that their stock is breeding efficiently and allow for monitoring in case something is going wrong to avoid potential injuries. Given that breeding activity can occur 24 hours a day, catching such mating is not always easy. However, data from past matings can provide improved probability of choosing the correct time periods. For example, if the breeding activity data shows that 40% of matings occur between the hours of 4 and 6 am, and the remaining spread over the rest of the 24 hour period, the farmer can plan to observe the herd around the period of 4 to 6 am.

Alternatively where data is downloaded to the herd management system in real time, for example when breeding activities are in progress, the herd management system could be provided with an alarm or alert functionality to notify the farmer, for example via an alert message sent via a messaging service to a mobile phone or other network accessible device, to tell the farmer to action a visual inspection. The herd management system could then alert the farmer if the breeding activity meets some criteria of interest to the farmer to warrant a visual inspection. An example of a breeding activity of interest to the farmer may be evidence of several breeders being in heat simultaneously, thus giving a high likelihood of the farmer being able to observe the bulls servicing the breeders and any associated aggressive behaviour. An alert in this situation could be triggered by breeding events such as several breeders being serviced within a given time period.

Embodiments of the breeding activity monitor also incorporating locating functionality, such as a GPS technology, are envisaged. For example a locating unit including GPS and wireless telecommunication technology could be programmed to transmit information to the herd management system when breeding activity occurs. In such embodiments an alert message may also include information regarding the location of the herd based on the present bull location determined from a GPS reading taken at the time the breeding activity occurred, or as tracked by the herd management system. Alternatively where the herd management system can track the location of the herd based on where data has been read from the breeding activity monitors, for example using data readers positioned at gates or watering holes and linked to a farm network, the herd management system may indicate the approximate location of the herd, such as a paddock location, based on this information. Independent of specific alerts the farmer may use the herd management system to find out where the herd is based on stored location tracking information or sending a query to one or more a breeding activity monitors via a telecommunication or farm network to determine the location of the herd.

Although the preferred embodiment describes using the herd management system in conjunction with breeding activity monitors carried by the male animals in the herd to collect the breeding activity data for analysis, it is also envisaged that breeding activity data acquired from other sources, such as other types of breeding activity monitoring or observation records could be input to the herd management system for analysis. The accuracy of predictions and modelling produced by the herd management system will, like all statistical analysis, vary with the accuracy and quantity of data provided. It is envisaged that embodiments of the herd management system could provide indications of statistical accuracy of predictions based on the source, quality and quantity of input breeding activity data.

The herd breeding and management system enables a farmer to maintain a large quantity of data for the herd for current and past breeding seasons which can be used to make management decisions in relation to the herd. The herd management system can perform statistical analysis on the overall herd or provide animal specific information.

For example, if the farmer wishes to increase or decrease the size of the herd, information regarding the work rates of current bulls or fertility of breeders the may be analysed to provide information regarding optimum herd size and bull to breeder ratio based on the current herd, and to predict productivity changes if this ratio were altered. The herd management system may also provide information regarding required number of breeders required to meet the optimum breeder to bull ratio and/or the required characteristics of additional bulls to service the herd. If a farmer needs to reduce the size of the herd the herd management system can provide data individually identifying the less fertile animals for culling. The herd management system may also model the impact of changes such as culling a percentage of unproductive animals from the herd and replacing them with newly purchased animals. Where the fertility characteristics of the desired replacement animals are known this information may be applied in the modelling process. If the fertility characteristics for the replacement animals are not known statistical norms may be used in the model to predict the impact on the herd productivity.

Information external to the breeding activity can also be used for this analysis. For example, profit/loss estimates for a breeding season based on the number of offspring expected, present size and make up of the herd, costs for maintaining the herd (i.e. feed, vet services, farm amenities, transport, etc) and the anticipated sale price for the offspring can be provided. Where fertility data is available for bulls the farmer may consider purchasing this data and also feeding it into the herd management system to model the impact on herd productivity to assist the farmer in making decisions such as the number of bulls to purchase, and/or which particular bull or bulls are most cost effective to purchase, to achieve the desired productivity increase for the least capital expenditure.

The herd management system can also analyse historical and current breeding data for the herd to model the impact of proposed changes to provide the farmer with estimates on the impact on the business for particular changes. For example, predicting the impact on the herd productivity during a drought based on historic data such as impact on fertility rates or effect of culling during previous droughts.

The herd management system may also be utilised in relation to other farm management decisions, for example pasture management. The herd management system may be used for modelling when to move the cows and planning pasture rotation based on how long pastures need to recover after grazing periods. The farmer can use the herd management system to anticipate what changes may need to be made when the herd size is increased or decreased or in drought conditions for example to avoid degradation of the land due to overgrazing or to decide when extra fodder needs to be provided. As the herd management system can alert the farmer to indicators of widespread fertility problems, such as changes in oestrus cycles of many breeders or reduction in number of conceptions in a season, which may be the result of malnutrition or environmental factors, this information could be taken into consideration in pasture management planning. Alternatively location tracking can be used to identity potential locations to investigate for environmental problems, such as areas to test for pollutants.

Although the preferred embodiment of the invention has been described in relation to application for monitoring a herd of cattle, embodiments of the invention may similarly be applied for other stock animals such as sheep, horses, pigs, deer, alpacas, goats etc.

In the claims which follow and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art, in Australia or any other country.

The invention claimed is:

1. A system for livestock breeding and management for use in a herd where each female animal carries a radio frequency identification (RFID) tag, the system comprising:
   a herd management system; and
   one or more breeding activity monitors to each be carried by a male animal, each breeding activity monitor adapted to:
   (i) detect when the male animal is mounting a female animal based on the body position of the male animal;
   (ii) read identification data from the RFID tag carried by the mounted female animal; and
   (iii) generate breeding activity data including the identification data of the mounted female animal and timing data for each mounting for output to the herd management system,
   wherein the herd management system is adapted to process breeding activity data output from the one or more breeding activity monitors to generate herd management data; and
   wherein the processing of the breeding activity data provides herd management data comprising conception data for each female animal including the indication whether or not the female animal is pregnant and wherein the conception data for each female is based on analysis of the mounting activity for the female animal and oestrus cycle data for the female animal, and one or more of:
   birth date estimates for each pregnant female animal;
   conception success rate data for each male animal;
   fertility and ease of impregnation data for each female animal; and
   offspring family data.

2. A system as claimed in claim 1 wherein each breeding activity monitor is provided with a wireless communication interface whereby the breeding activity data is transmitted to the herd management system for processing.

3. A system as claim in claim 2 further comprising one or more wireless base stations located in an area where the herd roams such that, when a breeding activity monitor is within transmission range of a base station, breeding activity data is transmitted wirelessly to the base station for subsequent transmission to the herd management system.

4. A system as claimed in claim 2 wherein each base station stores breeding activity data for subsequent downloading by a farmer.

5. A system as claimed in claim 3 wherein each base station transmits the breeding activity data to the herd management system via a communication network.

6. A system as claimed in claim 3 wherein each base station stores breeding activity data for subsequent downloading by a farmer.

7. The system according to claim 1, wherein the breeding activity monitor adapted to be carried by an animal comprises:
   a radio frequency identification (RFID) tag reader for reading identification data from an RFID tag secured to another animal in the herd;
   a mount detector to determine when the animal is mounting another animal based on the body position of the animal;
   a processor for processing the data from the RFID tag reader, processing data from the mount detector to generate breeding activity data including the identification data of the mounted animal and timing data for each breeding activity; and
   a communication interface to enable output of the acquired breeding activity data by an external device.

8. The system according to claim 7, wherein the mount detector determines whether the animal carrying the monitor is mounting another animal based on the body angle of the animal and motion of the animal.

9. The system according to claim 8, wherein the determination of mounting is further based on the proximity of the RFID tag reader to the RFID tag on the mounted animal.

10. The system according to claim 7, wherein the mount detector determines whether the animal carrying the monitor is mounting another animal based on the RFID tag on the mounted animal being within a predetermined arc of the range of the REID tag reader.

11. A method for monitoring breeding activity in a herd where each female animal carries a radio frequency identification (RFID) tag, the method comprising the steps of:
attaching a breeding activity monitor to be carried by the animal to each breeding male animal in the herd;
detecting by the breeding activity monitor attached when the male animal mounts a female animal based on the body position of the male animal;
for each mount:
reading identification data from the RFID tag of the mounted female animal; and
generating breeding activity data including the identification data for the mounted female animal and timing data for the mounting, and;
processing the breeding activity data output from one or more breeding data activity monitors to generate herd management data comprising conception data for each female animal including an indication whether or not each female animal is pregnant, wherein the conception data for each female animal is based on analysis of the mounting activity for the female animal and oestrus cycle data for the female animal, and one or more of:
birth date estimates for each pregnant female animal;
conception success rates for each male animal;
fertility and ease of impregnation data for each female animal; and
offspring family data.

12. A method as claimed in claim 11 wherein where breeding activity data indicates no available male animal has mounted the female animal within a duration longer than one oestrus cycle since a mounting of the female animal, the conception data for the female animal is updated to indicate likelihood of conception.

13. The method according to claim 11, where the birth date estimate for a pregnant female animal is determined based on a dates of mountings for the female animal by one or more male animals prior to conception being determined and a typical gestation period for the breed of animal.

14. The method according to claim 11, wherein a measure of the ease of impregnation of a female animal is provided based on the number of mountings by a male animal prior to conception.

15. A method as claimed in claim 14 wherein the measure of the fertility of a female animal is further based on fertility information for a male animal which impregnated the female animal.

16. A method as claimed in claim 11 wherein a measure of the fertility of a female animal is provided based on the number of oestrus cycles experienced by the female animal and the number of mountings between the birth of one offspring and the conception of another offspring.

17. A method as claimed in claim 16 wherein the measure of the fertility of a female animal is further based on fertility information for a male animal which impregnated the female animal.

18. The method according to claim 11, wherein a male animal work rate is determined based on the number of female animals being mounted by the male animal during a given period.

19. A method as claimed in claim 18 wherein the male animal work rate is further determined based on the number of female animals impregnated by the male animal during the given period.

20. The method according to claim 11, wherein a male animal conception rate is determined based on the number of female animals impregnated by the male animal during a given period.

21. The method according to claim 11, wherein offspring family data is based on the identification data for the female animal and the identity of one or more male animals mounting the female animal prior to conception being determined.

22. A method for analysing breeding activity data to provide herd management data comprising the steps of:
acquiring breeding activity data consisting of mounting data for a herd including for each mounting at least identification data for the mounted female animal and timing data;
analysing the breeding activity data to determine conception data for each female animal, including an indication whether or not the female animal is pregnant, wherein the conception data for each female animal is based on analysis of the mounting activity for the female animal and oestrus cycle data for the female animal, and one or more of:
birth date estimates for each pregnant female animal;
conception success rate data for each male animal;
fertility and ease of impregnation data for each female animal; and
offspring family data, and, and wherein the acquiring is performed by interrogation of RFID tags mounted to the female animals of the herd.

23. A herd management system for analysing breeding activity data including mounting data including for each mounting at least identification data for the mounted female animal and timing data, the system comprising:
an input interface adapted to enable at least breeding activity data to be manually or automatically entered into the system;
a processor adapted to process the input breeding activity data to produce herd management data;
a memory for storing breeding activity data and herd management data; and
an output interface,
wherein the processing of the breeding activity data provides herd management data comprising conception data for each female animal including an indication whether or not each female animal is pregnant, wherein the conception data for each female animal is based on analysis of the mounting activity for the female animal and oestrus cycle data for the female animal, and one or more of:
birth date estimates for each pregnant female animal;
conception success rate data for each male animal;
fertility and ease of impregnation data for each female animal; and
offspring family data.

24. A system as claimed in claim 23 wherein the processor is adapted to analyse data related to aspects of herd management other than breeding activity in conjunction with breeding activity data or herd management data.

* * * * *